United States Patent
Fink et al.

(10) Patent No.: US 7,679,988 B2
(45) Date of Patent: Mar. 16, 2010

(54) SOUND-WAVE IMAGING METHOD AND APPARATUS

(75) Inventors: Mathias Fink, Meudon (FR); Gabriel Montaldo, Paris (FR); Mickael Tanter, Paris (FR)

(73) Assignees: Centre National de la Recherche Scientifique -CNRS-, Paris Cedex (FR); universite Paris 7 - Denis Diderot, Paris Cedex (FR)

( * ) Notice: Subject to any disclaimer, the term of this patent is extended or adjusted under 35 U.S.C. 154(b) by 687 days.

(21) Appl. No.: 10/565,617

(22) PCT Filed: Jul. 23, 2004

(86) PCT No.: PCT/FR2004/001980

§ 371 (c)(1),
(2), (4) Date: Feb. 28, 2007

(87) PCT Pub. No.: WO2005/015540

PCT Pub. Date: Feb. 17, 2005

(65) Prior Publication Data

US 2007/0274156 A1    Nov. 29, 2007

(30) Foreign Application Priority Data

Jul. 25, 2003  (FR) .................................. 03 09140

(51) Int. Cl.
*G03B 42/06* (2006.01)
(52) U.S. Cl. ....................................................... 367/11
(58) Field of Classification Search ............ 367/81–191
See application file for complete search history.

(56) References Cited

U.S. PATENT DOCUMENTS

| 5,207,214 | A  | * | 5/1993 | Romano ........................ 601/4 |
| 6,198,829 | B1 |   | 3/2001 | Fink et al. |
| 2002/0126577 | A1 | * | 9/2002 | Borchardt .................... 367/88 |
| 2004/0257912 | A1 | * | 12/2004 | Dubinsky et al. ............. 367/81 |

FOREIGN PATENT DOCUMENTS

| WO | WO 97/03438 | | 1/1997 |
| WO | WO2005013675 | * | 11/2005 |

OTHER PUBLICATIONS

Babriel Montaldo et al, Generation of very high pressure pulses with 1-bit time reversal in a solid waveguide, Dec. 2001, 2001 Acoustical Society of America pp. 2849-2857.*

(Continued)

*Primary Examiner*—Thomas H Tarcza
*Assistant Examiner*—Luke D Ratcliffe
(74) *Attorney, Agent, or Firm*—Miller, Matthias & Hull

(57) ABSTRACT

An ultrasound imaging method including an emission step during which an array of transducers is caused to emit at an ultrasound wave focused in a target medium by causing the excitation wave to pass through a reverberant solid object prior to reaching the target medium.

30 Claims, 1 Drawing Sheet

OTHER PUBLICATIONS

Derode et al., "Random Multiple Scattering of Ultrasound. II. Is Time Reversal a Self-Averaging Process?" Physical Review (Statistical, Nonlinear, and Soft Matter Physics), vol. 64, No. 3, pp. 036606/1-13, (Sep. 2001).

Derode et al., "Generation of Very High Pressure Pulses with 1-bit Time Reversal in a Solid Waveguide," Journal of the Acoustical Society of America, vol. 110, No. 6, pp. 2849-2857, (Dec. 2001).

Yon et al., "Sound Focusing in Rooms: the Time-Reversal Approach," Journal of the Acoustical Society of America, vol. 113, No. 3, pp. 1533-1543, (Mar. 2003).

French Preliminary Search Report FR 0309140; report dated May 11, 2004.

International Search Report PCT/FR2004/001980; report dated Jan. 14, 2005.

* cited by examiner

US 7,679,988 B2

SOUND-WAVE IMAGING METHOD AND APPARATUS

CROSS-REFERENCE TO RELATED APPLICATION

This is the U.S. National Phase of International Application No. PCT/FR2004/01980 filed 23 Jul. 2004, the entire disclosure of which is incorporated herein by reference.

BACKGROUND OF THE INVENTION

The present invention relates to methods and apparatuses for imaging by sound waves.

More particularly, the invention relates to a sound-wave imaging method including at least one emission step during which a first array of transducers (comprising at least one transducer) is caused to emit at least one ultrasound excitation wave presenting a certain central emission frequency $f_c$ and focused on at least one target point in a target medium, and said excitation wave is caused to pass through a reverberant medium prior to reaching the target medium.

Document WO-A-97/03438 describes a method of this type that gives complete satisfaction.

A particular object of the present invention is to further improve that known method in order to make it easier to use, in particular for medical or industrial applications.

To this end, according to the invention, a method of the kind in question is characterized in that during the emission step, a reverberant solid object is used as the reverberant medium, with each transducer of the first array being secured thereto, said reverberant solid object being adapted to give rise to multiple reflections of the excitation wave that passes therethrough and to cause an impulse wave of duration $1/f_c$ entering into said solid object to lead to sound emission to the target medium taking place over a duration of not less than $10/f_c$.

SUMMARY OF THE INVENTION

By means of these dispositions, the reverberant object and the first array of transducers together form a one-piece probe in which the transducers of the first array are positioned accurately in advance, thus avoiding or greatly reducing adjustments on each use. In addition, when the reverberant solid object is of small size and light weight, the probe is easy to handle, without upsetting the positioning of the transducers.

In various implementations of the method of the invention, recourse may optionally also be had to one or more of the following dispositions:

during the emission step, the excitation wave s(t) is emitted towards a number K not less than 1 of predetermined target points k belonging to the target medium, by causing each transducer i of the first array to emit an emission signal:

$$s_i(t) = \sum_{k=1}^{K} e_{ik}(t) \otimes s(t)$$

where the signals $e_{ik}(t)$ are predetermined individual emission signals adapted so that when the transducers i emit the signals $e_{ik}(t)$, an impulse sound wave is generated at the target point k;

the signals $e_{ik}(t)$ are encoded on a number of bits lying in the range 1 to 64;

the signals $e_{ik}(t)$ are coded on 1 bit;

the individual emission signals $e_{ik}(t)$ are determined experimentally during a training step, prior to said emission step;

during the training step, an ultrasound impulse signal is caused to be emitted successively from each predetermined target point k, the signals $r_{ik}(t)$ received by each of the transducers i of the first array from the emission of said ultrasound impulse signal are picked up, and the individual emission signals $e_{ik}(t)$ are determined by time reversal of the received signals $r_{ik}(t)$:

$$e_{ik}(t)=r_{ik}(-t);$$

during the training step, a liquid medium different from the target medium is put into contact with the reverberant solid object, and said impulse signal is caused to be emitted from said liquid medium;

during the training step, for a predetermined target point k, an ultrasound impulse signal is caused to be emitted in succession from each of the transducers i of the first array, the signals $r_{ik}(t)$ received at the target point k from the emission of said ultrasound impulse signals are picked up, and the individual emission signals $e_{ik}(t)$ are determined by time reversal of the received signals $r_{ik}(t)$:

$$e_{ik}(t)=r_{ik}(-t)$$

during the training step, a liquid medium different from the target medium is put into contact with the reverberant solid object, and the signals $r_{ik}(t)$ are picked up in said liquid medium;

the liquid medium used during the training step essentially comprises water, and during the emission step, the target medium in which the excitation wave is focused comprises at least a portion of the body of a patient;

the individual emission signals $e_{ik}(t)$ are determined by calculation;

the reverberant solid object through which the excitation wave is caused to pass during the emission step is in contact with the target medium;

the method further comprises a step of receiving echoes emitted by the target medium in response to the excitation wave, in order to image at least a portion of said target medium;

the excitation wave is emitted for a duration lying in the range $\frac{1}{2}f_c$ to $10/f_c$;

during the emission step, the excitation wave passes through at least one acoustically non-linear medium and presents an amplitude that is sufficient for waves that are harmonics of the central emission frequency to be generated in said acoustically non-linear medium; and during the reception step, echoes returned from the target medium are picked up at a receive frequency that is an integer multiple of the central emission frequency;

the harmonic waves are generated in the target medium, which presents non-linear acoustic behavior;

during the reception step, the echoes returning from the target zone are picked up at a receive frequency equal to two or three times the central emission frequency;

during the emission step, the target medium in which the excitation wave is focused comprises at least a portion of the body of a patient;

during the reception step, the echoes returning from the target zone are picked up by means of a second array of transducers secured to said reverberant solid object;

during the emission step, an amplitude modulated excitation wave is emitted that is adapted to apply radiation pressure on the target medium to generate a low frequency shear wave; and during the emission step, an excitation wave is emitted that is adapted to heat the target medium locally.

Furthermore, the invention also provides a sound-wave imaging apparatus comprising at least emitter means comprising a first array of transducers, said emitter means being adapted to cause at least one ultrasound excitation wave to be emitted by the first array of transducers through a reverberant medium, the emitted wave presenting a certain central emission frequency $f_c$ and being focused on at least one target point of a target medium, the apparatus being characterized in that the reverberant medium comprises a reverberant solid object having each of the transducers of the first array secured thereto, said reverberant solid object being adapted to give rise to multiple reflections of the excitation wave passing therethrough and to cause an impulse wave of duration $1/f_c$ entering said solid object to lead to sound being emitted towards the target medium over a duration of not less than $10/f_c$.

In various embodiments of the apparatus of the invention, recourse may optionally also be had to one or more of the following dispositions:

the emitter means are adapted to cause the excitation wave $s(t)$ to be emitted to a number K not less than 1 of predetermined target points k belong to the target medium, by causing each transducer i of the first array to emit an emission signal:

$$s_i(t) = \sum_{k=1}^{K} e_{ik}(t) \otimes s(t)$$

where the signals $e_{ik}(t)$ are predetermined individual emission signals adapted so that when the transducers i emit the signals $e_{ik}(t)$, an impulse sound wave is generated at the target point k;

the apparatus further comprises receiver means for receiving echoes emitted by the target medium in response to the excitation wave in order to image at least a portion of said target medium;

the emitter means are adapted to emit the excitation wave for a duration lying in the range $\frac{1}{2}f_c$ to $10/f_c$;

the receiver means are adapted to receive the echoes returning from the target medium at a receive frequency that is an integer multiple of the central emission frequency;

the receiver means are adapted to receive the echoes returning from the target medium at a receive frequency equal to twice the central emission frequency;

the receiver means comprise a second array of transducers secured to said reverberant solid object;

the emitter means are adapted to emit an excitation wave adapted to apply radiation pressure on the target medium; and the emitter means are adapted to emit an excitation wave adapted to heat the target medium locally.

Other characteristics and advantages of the invention appear from the following description of its implementations, given by way of non-limiting example and with reference to the accompanying drawing.

DESCRIPTION OF PREFERRED EMBODIMENTS

Figure 1:
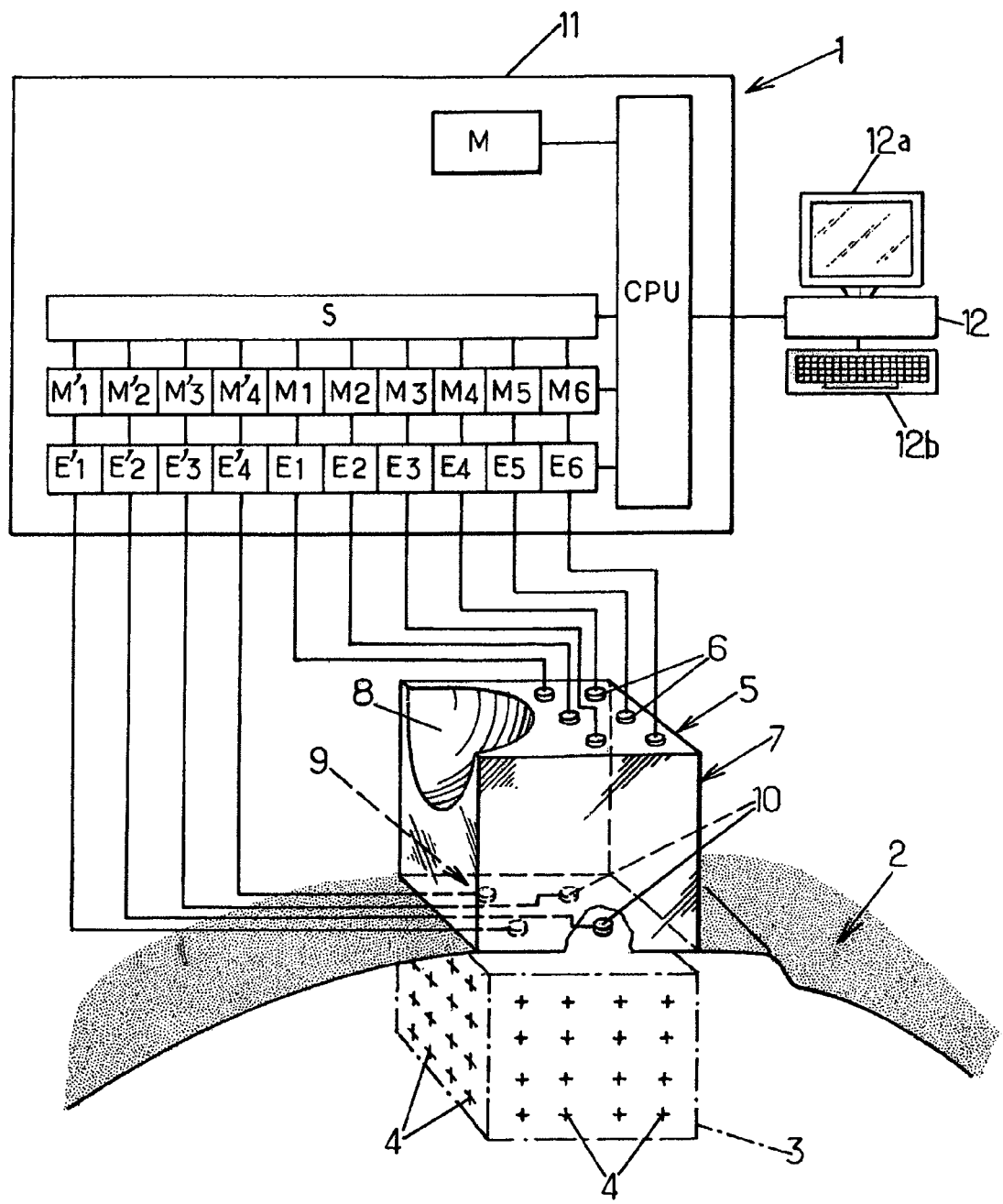
FIG. 1 is a diagrammatic view showing apparatus for focusing ultrasound waves in an embodiment of the invention.

The ultrasound wave focusing apparatus 1 shown in the figure is intended for example for imaging a target medium 2, e.g. a portion of the body of a patient in a medical application, or indeed a portion of an industrial article in non-destructive or other inspection applications.

More precisely, the ultrasound wave focusing apparatus 1 is for imaging a zone 3 under examination in the target medium 2, said zone 3 possibly being three-dimensional.

For this purpose, the imaging apparatus 1 is adapted to emit a succession of ultrasound excitation waves focused on different predetermined target points 4 belonging to the zone 3. After emitting each excitation wave, the imaging apparatus picks up the echoes emitted by the target zone in response to said excitation waves, preferably by focusing in reception also on the point 4 on which the excitation wave was focused.

The excitation waves are emitted by a first array 5 of emission transducers 6, which are secured to a reverberant solid object 7 adapted so that the excitation waves emitted by said first array 5 of transducers are subjected to multiple reflections inside said solid object prior to reaching the target medium 2, which is placed in contact with said solid object 7.

The emission transducers 6 may be of any number lying in the range one to several tens, e.g. about one hundred, and passing via intermediate values such as a number lying in the range five to ten as in the example shown in FIG. 1.

In the example described, the object 7 can be constituted by a block of metal or some other rigid material in which ultrasound waves propagate with very little attenuation and with long reverberation times, such that an impulse wave of duration $1/f_c$ emitted by the first array 5 of transducers leads to sound being emitted into the target medium 2 over a duration of not less than $10/f_c$.

In the example described herein, the object 7 is generally in the shape of a rectangular parallelepiped having a recess 8 formed therein having the shape of a portion of a sphere, the transducers 6 of the first array being, for example, stuck on the face of the object 7 that is situated remote from the face of said object that is to come into contact with the target medium 2.

Naturally, other general shapes could be envisaged for the object 7 and/or the recess 8.

The echoes returning from the target zone 3 after the emission of an excitation wave that is focused on one of the target points 4 are themselves picked up by a second array 9 of receiver transducers 10, which receiver transducers may optionally also be secured to the above-mentioned object 7, e.g. on the face of said object that is in contact with the target medium 2.

The receiver transducers may be of any number, lying in the range one to several tens (these transducers are four in number in the particular example shown in FIG. 1).

The transducers 6, 10 are controlled independently of one another by a microcomputer 12 (conventionally provided with user interfaces such as a screen 12a and a keyboard 12b), possibly via a central processor unit CPU contained for example in an electronics rack 11 connected via a flexible cable to the transducers 6, 10.

By way of example, the electronics rack 11 may comprise:

respective sampler circuits E1-E6; E'1-E'4 connected to each of the transducers 6, 10;

respective memories M1-M6; M'1-M'4 connected to the samplers of each of the transducers 6, 10;

a summing circuit S connected to the memories M1-M6; M'1-M'4; and a general memory M connected to the central processor unit CPU.

The above-described apparatus operates as follows.

Prior to any imaging operation, a matrix of individual emission signals $e_{ik}(t)$ is initially determined in such a manner that in order to generate an excitation wave s(t) at a target point k, each transducer i in the first array 5 is caused to emit an emission signal:

$$s_i(t) = e_{ik}(t) \otimes s(t)$$

The individual emission signals may optionally be determined by calculation (e.g. by a space-time reversal filter method), or they may be determined experimentally during a preliminary training step.

During this training step, an ultrasound impulse signal may advantageously be emitted by an emitter such as a hydrophone placed successively at each target point k; and the signals $r_{ik}(t)$ received by each of the transducers i in the first array 5 on the basis of the emission of said ultrasound impulse signal are picked up. The signals $r_{ik}(t)$ picked up in this way are forwarded to the CPU, which then calculates the individual emission signals $e_{ik}(t)$ by time reversal of said received signals:

$$e_{ik}(t) = r_{ik}(-t)$$

If the target medium 2 is a liquid medium, it may perhaps be possible to proceed with the preliminary training step by positioning the ultrasound wave emitter in succession at the various target points 4 in the zone 3 to be examined. If the medium 2 is a portion of the body of a patient or a similar medium comprising a large quantity of water, it may be possible to proceed with the training stage by replacing the medium 2 with a volume of liquid that preferably comprises a majority of water, and successively positioning the ultrasound wave emitter at the locations of the various target points 4, in positions identified relative to the reverberant solid object 7.

By taking advantage of the three-dimensional reciprocity principle, it is also possible to determine the signals $e_{ik}(t)$ by placing one or more hydrophones successively at the target points k in the above-mentioned liquid medium. For each hydrophone position k, an ultrasound impulse signal is caused to be emitted in succession by each of the transducers i, and the signals $r_{ik}(t)$ are picked up by the hydrophone. Thereafter, the signals $e_{ik}(t)$ are deduced by time reversal:

$$e_{ik}(t) = r_{ik}(-t)$$

Thereafter, when it is desired to image the zone 3 for examination in the target medium 2, the reverberant solid object 7 is put into contact with the target medium, and the transducers 6 of the first array are caused to emit a succession of excitation waves each localized on one of the target points 4 of the zone 3 to be examined.

For this purpose, in order to focus an excitation wave on a target point k, each transducer i of the first array 5 is caused to emit an emission signal:

$$s_i(t) = e_{ik}(t) \otimes s(t)$$

This operation of emitting an excitation wave is repeated for each of the target points 4 in the zone 3 for examination.

In a variant, it is also possible to generate an excitation wave s(t) that is focused on a number K of target points 4 in the zone 3 for examination, where K is greater than 1, by causing each transducer i of the first array 5 to emit an emission signal:

$$s_i(t) = \sum_{k=1}^{K} e_{ik}(t) \otimes s(t)$$

The excitation waves as emitted in this way presents a central frequency that can lie in particular in the range 200 kilohertz (kHz) to 100 megahertz (MHz), e.g. at 3 MHz, and these excitation waves are emitted by the transducers 6 of the first array for a duration lying in the range $\frac{1}{2}f_c$ to $10/f_c$.

After each emission of an excitation wave focused on one or more target points 4 of the zone 3 for examination, the echoes returned by the target medium 2 are picked up by means of the receiver transducers 10 of the second array 9. The signals as picked up in this way are digitized by the samplers E'1-E'4 and stored in the memories M'1-M'4, and then processed by a conventional channel-forming technique implementing reception focusing on the emission target point(s) 4.

The processing in question, which consists in particular in picking up the signals and in applying differing delays to the signals as picked up, can be implemented by the summing circuit S.

Advantageously, during this step of receiving the echoes, advantage can be taken of the non-linear acoustic behavior of at least one of the materials through which the excitation wave passes, i.e. the target medium 2 and/or the reverberant solid object 7 (in practice, it is mainly the target medium 2 that will present non-linear acoustic behavior, since the material of the reverberant solid object preferably presents acoustic behavior that is linear). The excitation wave is generated at an amplitude that is sufficient for waves that are harmonics of the central frequency $f_c$ to be generated at a level that is sufficient for it to be possible to receive the echoes returning from the target medium 2 at a receive frequency that is an integer multiple of the central emission frequency $f_c$.

Advantageously, echoes returning from the target medium 2 at a frequency that is two or three times the frequency $f_c$ are thus received.

Such frequency-selective reception can be obtained either by the very structure of the receiver transducers 10, in known manner, or else by frequency filtering the signals coming from the receiver transducers 10.

By receiving in this way at a frequency that is different from the frequency $f_c$, reception is not disturbed in any way by the excitation wave itself, even though this excitation wave is of particularly long duration because of the multiple reflections inside the reverberant solid object 7.

Although the apparatus 1 is described above as being an ultrasound imaging apparatus, where appropriate, in addition to imaging or independently of imaging, the apparatus could be used for the purposes of:

generating a shear wave in the target medium 2; or locating heating the target medium.

In order to generate a shear wave, e.g. in order to proceed with imaging followed by propagating the shear wave, in particular as described in document FR-A-2 791 136 or in French patent application No. 02/10838, the above-mentioned ultrasound excitation wave s(t) can be emitted over a relatively long duration, e.g. lying in the range $10/f_c$ to 200,000/$f_c$ with (continuous or stepwise) amplitude modulation enabling radiation pressure to be applied on the target medium 2 in order to generate the shear wave.

Alternatively, when the purpose is to heat the target medium 2 locally, the emission transducers 6 may emit the above-mentioned ultrasound excitation wave s(t) (continuously or otherwise) for a duration longer than 0.5 seconds (s), and preferably over a broad frequency band. This generates a temperature rise in the medium 2 that may lie in the range a few degrees to a few tens of degrees.

It should be observed that the method and the apparatus of the invention could also be used for precision ultrasound cleaning applications or for ultrasound welding applications.

The invention claimed is:

1. A sound-wave imaging method, comprising:
    at least one emission step during which a first array of transducers is caused to emit at least one ultrasound excitation wave presenting a certain central emission frequency $f_c$ and focused on at least one target point in a target medium, and said excitation wave is caused to pass through a reverberant solid object prior to reaching the target medium,
    each transducer of the first array being secured to said reverberant solid object and said reverberant solid object being adapted to give rise to multiple reflections of the excitation wave that passes therethrough and to cause an impulse wave of duration $1/f_c$ entering into said solid object to lead to sound emission to the target medium taking place over a duration of not less than $10/f_c$;
    at least a reception step wherein echoes emitted by the target medium in response to the excitation wave are received; and
    an imaging step wherein an image of at least a portion of said target medium is built based on the received echoes.

2. The method according to claim 1, in which during the emission step, the excitation wave s(t) is emitted towards a number K not less than 1 of predetermined target points k belonging to the target medium, by causing each transducer i of the first array to emit an emission signal:

$$s_i(t) = \sum_{k=1}^{K} e_{ik}(t) \otimes s(t)$$

where the signals eik(t) are predetermined individual emission signals adapted so that when the transducers i emit the signals eik(t), an impulse sound wave is generated at the target point k.

3. The method according to claim 2, in which the signals eik(t) are encoded on a number of bits lying in the range 1 to 64.

4. The method according to claim 3, in which the signals eik(t) are coded on 1 bit.

5. The method according to claim 2, in which the individual emission signals eik(t) are determined experimentally during a training step, prior to said emission step.

6. The method according to claim 5, in which during the training step, an ultrasound impulse signal is caused to be emitted successively from each predetermined target point k, the signals rik(t) received by each of the transducers i of the first array from the emission of said ultrasound impulse signal are picked up, and the individual emission signals eik(t) are determined by time reversal of the received signals rik(t):

$$e_{ik}(t)=r_{ik}(-t).$$

7. The method according to claim 6, in which, during the training step, a liquid medium different from the target medium is put into contact with the reverberant solid object, and said impulse signal is caused to be emitted from said liquid medium.

8. The method according to claim 5, in which, during the training step, for a predetermined target point k, an ultrasound impulse signal is caused to be emitted in succession from each of the transducers i of the first array, the signals rik(t) received at the target point k from the emission of said ultrasound impulse signals are picked up, and the individual emission signals eik(t) are determined by time reversal of the received signals rik(t):

$$e_{ik}(t)=r_{ik}(-t).$$

9. The method according to claim 8, in which, during the training step, a liquid medium different from the target medium is put into contact with the reverberant solid object, and the signals rik(t) are picked up in said liquid medium.

10. The method according to claim 7, in which the liquid medium used during the training step essentially comprises water, and in which during the emission step, the target medium in which the excitation wave is focused comprises at least a portion of the body of a patient.

11. The method according to claim 2, in which the individual emission signals eik(t) are determined by calculation.

12. The method according to claim 1, in which the reverberant solid object through which the excitation wave is caused to pass during the emission step is in contact with the target medium.

13. The method according to claim 1, further comprising a step of receiving echoes emitted by the target medium in response to the excitation wave, in order to image at least a portion of said target medium.

14. The method according to claim 1, in which the excitation wave is emitted for a duration lying in the range $½f_c$ to $10/f_c$.

15. The method according to claim 1, in which:
    during the emission step, the excitation wave passes through at least one acoustically non-linear medium and presents an amplitude that is sufficient for waves that are harmonics of the central emission frequency to be generated in said acoustically non-linear medium; and
    during the reception step, echoes returned from the target medium are picked up selectively at a receive frequency that is an integer multiple of the central emission frequency.

16. The method according to claim 15, in which the harmonic waves are generated in the target medium, which presents non-linear acoustic behavior.

17. The method according to claim 15, in which, during the reception step, the echoes returning from the target zone are picked up selectively at a receive frequency equal to two or three times the central emission frequency.

18. The method according to claim 1, in which, during the emission step, the target medium in which the excitation wave is focused comprises at least a portion of the body of a patient.

19. The method according to claim 1, in which, during the reception step, the echoes returning from the target zone are picked up by means of a second array of transducers secured to said reverberant solid object.

20. The method according to claim 1, in which, during the emission step, an amplitude modulated excitation wave is emitted that is adapted to apply radiation pressure on the target medium to generate a low frequency shear wave.

21. The method according to claim 20, in which, during the emission step, the target medium in which the excitation wave is focused, comprises at least a portion of the body of a patient.

22. The method according to claim 1, in which, during the emission step, an excitation wave is emitted that is adapted to heat the target medium locally.

23. A sound-wave imaging apparatus comprising at least:
    emitter means comprising a first array of transducers, said emitter means being adapted to cause at least one ultrasound excitation wave to be emitted by the first array of transducers through a reverberant solid object having the transducers of the first array secured thereto, the emitted wave presenting a certain central emission frequency $f_c$ and being focused on at least one target point of a target medium, said reverberant solid object being adapted to give rise to multiple reflections of the excitation wave passing therethrough and to cause an impulse wave of duration $1/f_c$ entering said solid object to lead to sound being emitted towards the target medium over a duration of not less than $10/f_c$;

receiver means for receiving echoes emitted by the target medium in response to the excitation wave, and;

imaging means for building an image of at least a portion of said target medium based on the received echoes.

24. Apparatus The apparatus according to claim 23, in which, the emitter means are adapted to cause the excitation wave s(t) to be emitted to a number K not less than 1 of predetermined target points k belong to the target medium, by causing each transducer i of the first array to emit an emission signal:

$$s_i(t) = \sum_{k=1}^{K} e_{ik}(t) \otimes s(t)$$

where the signals eik(t) are predetermined individual emission signals adapted so that when the transducers i emit the signals eik(t), an impulse sound wave is generated at the target point k.

25. The apparatus according to claim 23, in which the emitter means are adapted to emit the excitation wave for a duration lying in the range $\frac{1}{2}f_c$ to $10/f_c$.

26. The apparatus according to claim 23, in which the receiver means are adapted to receive the echoes returning from the target medium, selectively at a receive frequency that is an integer multiple of the central emission frequency.

27. The apparatus according to claim 26, in which the receiver means are adapted to receive the echoes returning from the target medium, selectively at a receive frequency equal to 2 or 3 times the central emission frequency.

28. The apparatus according to claim 25, in which the receiver means comprise a second array of transducers secured to said reverberant solid object.

29. The apparatus according to claim 23, in which the emitter means are adapted to emit an excitation wave adapted to apply radiation pressure on the target medium.

30. The apparatus according to claim 23, in which the emitter means are adapted to emit an excitation wave adapted to heat the target medium locally.

* * * * *